United States Patent [19]
Vanderhoeden

[11] 3,992,151
[45] Nov. 16, 1976

[54] METHOD FOR DETERMINING ALUMINUM HALIDE SOLUTION CONCENTRATIONS

[75] Inventor: Hans Vanderhoeden, Sarnia, Canada
[73] Assignee: Polysar Limited, Sarnia, Canada
[22] Filed: Aug. 19, 1975
[21] Appl. No.: 605,846

[30] Foreign Application Priority Data
Sept. 10, 1974  Canada .............................. 209008

[52] U.S. Cl. ........................... 23/230 R; 23/230 A; 23/253 R
[51] Int. Cl.² ........................................ G01N 31/16
[58] Field of Search ...................... 23/230 R, 230 A; 423/130, 135

[56] References Cited
UNITED STATES PATENTS

| | | | |
|---|---|---|---|
| 2,965,453 | 12/1960 | Harlan et al. ...................... | 23/230 R |
| 3,271,111 | 9/1966 | Boyd, Jr. et al. ................... | 23/230 R |
| 3,321,280 | 5/1967 | Trotter, Jr. et al. ............... | 23/230 R |
| 3,537,820 | 11/1970 | Markant et al. ................... | 23/230 R |
| 3,556,730 | 1/1971 | Mitacek ............................ | 23/230 R |
| 3,653,835 | 4/1972 | Brandel ............................. | 23/230 R |

OTHER PUBLICATIONS
Khudyakova "Automatic Conductometric Analysis I, the Determination of HCl & ALCl₃," Chem. Abstr. vol. 55, 4243g.
Green et al. Determination of ALCl₃ & HCl in Hydrocarbon Streams," Anal. Chem. vol. 17, 1945, pp. 351–352.

*Primary Examiner*—Morris O. Wolk
*Assistant Examiner*—Arnold Turk
*Attorney, Agent, or Firm*—Stevens, Davis, Miller & Mosher

[57] ABSTRACT

A process for continuous monitoring of the concentration of an aluminum halide (e.g. aluminum trichloride) in solution in a volatile solvent (e.g. methylchloride) comprises contacting the solution with steam or hot water so as to flash off the solvent and hydrolyse the aluminum halide to an acid reaction product, neutralizing the reaction solution with alkali, measuring the volume of solvent flashed off and measuring the quantity of alkali necessary to maintain substantially neutral pH of the reaction products. From these measurements, continuous readings of aluminum halide concentration are obtainable. The process is especially useful in monitoring the aluminum chloride catalyst concentration in a butyl rubber polymerization facility.

7 Claims, 2 Drawing Figures

METHOD FOR DETERMINING ALUMINUM HALIDE SOLUTION CONCENTRATIONS

This invention relates to a process for determining the concentration of an aluminum halide dissolved in a volatile solvent.

In various processes in the chemical industry, solutions of aluminum halides in volatile solvents are used as reagents, catalysts, etc. For example, in the manufacture of butyl rubber, isobutylene and isoprene are copolymerized with a catalyst of aluminum trichloride dissolved in methyl chloride, at low temperatures (below about −70° C). The process is carried out continuously. The amount of aluminum trichloride catalyst used, in relation to the amount of monomers, has an effect on the properties of the final rubber which is produced. Consequently it is desirable to be able to monitor the concentration of aluminum trichloride in the catalyst solution, so as to be able to make the necessary adjustments, as the process continues. Previously proposed methods for continuous monitoring of aluminum halide concentrations in volatile solvents have included measurement of electrical conductivity of the solution, measurement of dielectric properties of the catalyst solution and automated colourimetric titration under pressure, but have not proved satisfactory.

The present invention provides a method for continuous aluminum halide concentration measurement, in solution in volatile solvents, based upon the principle that aluminum halides react with water to form acidic hydrogen halides. The amount of hydrogen halides so produced is proportional to the amount of aluminum halide reacted, and can be measured by titration with an alkali. By using hot water or steam to react with the aluminum halide in solution in a volatile solvent, the volatile solvent can be flashed off, collected and and its volume measured. Thus, a concentration of aluminum halide in the original solvent can be determined.

According to the present invention, therefore, there is provided a process for determining the concentration of an aluminum halide in a solution of the aluminum halide in a volatile solvent, which comprises:

bringing the solution continuously into contact with hot water or steam to form an acidic reaction product, the quantity and temperature of the hot water or steam being sufficient to volatilize the solvent;

contacting the reaction product continuously with an alkali; controlling and measuring the rate of supply of said alkali so as substantially to neutralize the acidic reaction product and maintain the pH of the resultant reaction mixture within the pH range from 6.5 to 7.5;

and measuring the quantity of solvent volatilized.

Preferably, the alkali is supplied as an aqueous alkali solution of predetermined concentration. From a knowledge of the concentration of the alkali in said aqueous alkali solution, the concentration of aluminum halide in the solution of aluminum halide in volatile solvent can be determined, based on measurements of the amount of alkali solution required to maintain a substantially constant pH in the reaction solution, and on measurements of the volume of solvent volatilized, duly corrected for temperature and pressure of measurement.

The process of the invention is suitable for measuring aluminum halide concentrations from about 0.05 gms. per 100 mls. solution to about 5 gms. per 100 mls. solution, with the preferred range being from 0.1 to 0.5 gms. per 100 mls. solution.

The amount of hot water or steam which contacts the cold aluminum halide solution must be sufficient to cause rapid volatilization (or flashing off) of the solvent. Such a quantity, in connection with solutions of the concentrations referred to above, is sufficient to hydrolyse all the aluminum halide in the solution being monitored.

The precise nature of the alkali solution which is used to contact the water-catalyst solution reaction product is not critical, provided that it is capable of rapid, quantitative neutralization of the acids generated. Aqueous solutions of caustic alkali (sodium hydroxide or potassium hydroxide) are preferred, but other aqueous alkali solutions, such as ammonium hydroxide, sodium carbonate, borax etc. can also be used.

The concentration of alkali solution used in the process of the present invention is predetermined, so that the amount of alkali used to maintain substantially neutral pH in the reaction solution can be determined. The actual desirable concentration to use depends upon the flow rates employed and the aluminum halide solution concentration, but will ordinarily be within the range 0.2 – 0.5 N, preferably 0.5 – 0.1 N.

Suitably, the aluminum halide solution, hot water or steam, and aqueous alkali solution are brought together and reacted in a reaction vessel, which may be in the form of an elongated tube. The temperature in the reaction vessel is suitably in the range 25°–90° C, and this can be adjusted by controlling the flow rates of the various reactant solutions. It is preferred that the temperature be maintained in the range 40°–80° C, most preferably from 50°–70° C. For convenience, the hot water of steam may be mixed with the aqueous alkali solution immediately prior to entering the reaction vessel, and introduced through a common port.

Halides of aluminum which can be used in the process of the present invention include aluminum trichloride, aluminum tribromide and aluminum triiodide. The preferred halides are aluminum trichloride and aluminum tribromide, with aluminum trichloride being most preferred. The invention is applicable to solutions of such aluminum halides in volatile solvents, which solvents can be vapourized, or flashed off, by the heat derived from low pressure steam. Such solvents include aliphatic, cyclo-aliphatic and aromatic hydrocarbons, alkyl halides, aryl halides, nitro derivatives of aliphatic and aromatic hydrocarbons, carbon disulphide and the like, the solvent in all cases being selected in conjunction with the particular aluminum halide under consideration, to ensure that a suitable solution of the aluminum halide in the solvent is formed.

Preferred among volatile solvents in the process of the present invention are butane, pentane, hexane, cyclopentane, benzene, toluene, methyl halides, ethyl halides, chlorobenzene, nitromethane, nitroethane, nitrobenzene, with the most preferred such solvents being butane, benzene, methyl chloride and ethyl chloride.

A particular specific application of the process according to the present invention is in the monitoring of the catalyst used in the polymerization of isobutylene with isoprene, to make butyl rubber. Such catalyst comprises a solution of aluminum trichloride in methyl chloride and is utilized at low temperatures, e.g. below about − 70° C. The invention will, therefore, be further described with reference to such a process, but it will be appreciated that the invention is by no means limited to such specific application.

A specific embodiment of the present invention will now be described in more detail, with reference to the accompanying drawings, in which.

In the drawings, like reference numerals indicate like parts.

Figure 1:
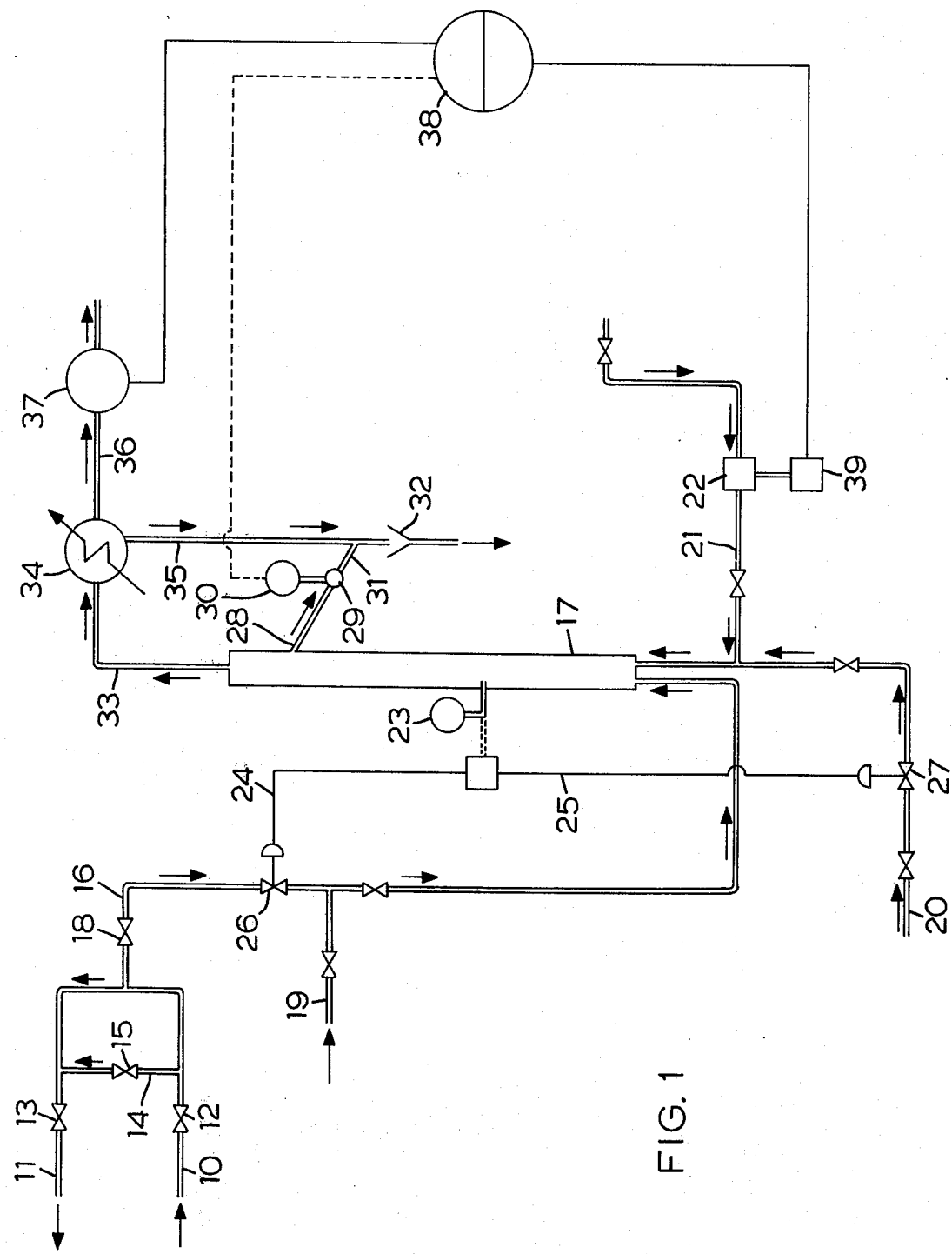
FIG. 1 is a diagrammatic process flow sheet illustrating a process scheme for carrying out the process of the present invention.

With reference to FIG. 1, the apparatus comprises a catalyst circulating line having an inflow branch 10, into which the solution flows from the butyl rubber polymerization facility, an outflow branch 11 through which some of the catalyst solution is returned to the butyl facility, the inflow and outflow branches being equipped with respective shut off valves 12, 13. The infow and outflow branches are interconnected by line 14 having a shut off valve 15 therein, and both branches interconnect with a lead-off line 16 which itself connects with a reaction vessel 17. Shut off valve 18 controls the flow of catalyst solution into line 16; opening of valve 18 and closing of valve 15 permits a stream of solution to enter line 16, whereas closing of valve 18 and opening of valve 15 permits the solution to recirculate back to the butyl facility.

Thae lead-off line 16 communicates with a nitrogen supply line 19, through which nitrogen can be supplied to the reaction vessel 17 as a safety measure.

There is also provided a low pressure steam line 20 communicating with reaction vessel 17, and having associated flow valves and flow control devices. There is further provided an alkali supply line 21 communicating with steam line 20 at a position adjacent to the point of communication of steam line 20 and reaction vessel 17. Thus, steam and alkali solution can be supplied to the reaction vessel 17.

A variable control pump 22 is provided in the alkali supply line 21. By this means, the rate of flow of alkali solution to reaction vessel 17 can be controlled and measured by the flow recording and control means 39.

The reaction vessel 17 takes the form of a upright elongated glass tube, with the lead-off line 16 supplying catalyst solution, the steam line 20 and the alkali supply line 21 all communicating with the bottom of the tube 17. At or about its mid-point, tube 17 is provided with a temperature sensing means 23, which is pre-set to ensure substantially constant temperature within tube 17 as the reaction proceeds. Temperature sensing means 23 is electrically connected via electrical lines 24, 25 to the shut-off control valve 26, in the lead-off line 16 supplying cold catalyst solution and to the flow control valve 27 in the steam line 20 supplying hot steam. Whilst some fluctuations in temperature inside vessel 17 are unimportant, substantially constant temperature is desirable to avoid waste of steam, and this can be achieved by control of relative flow rate of steam at the substantially constant flow rate of catalyst solution. In addition, temperature sensing means 23 is arranged to close off valve 26 in the event that the temperature in vessel 17 becomes much too high or much too low.

The reaction tube 17 near its upper end is provided with an outflow tube 28 communicating with a collection vessel 29. A pH measuring device 30 is connected to the collection vessel 29 for measuring pH of liquid collected in vessel 29. Vessel 29 is provided with an overflow tube 31 through which liquid is drained away to drain 32.

A gas outflow tube 33 communicates with the top of the reaction tube 17, and with a condenser means 34 whereby entrained water from the gas stream can be condensed. Liquid from the condenser means 34 is fed by a tube 35 to the drain 32. From condenser means 34, a further gas outflow tube 36 leads to a gas volume recording means 37. The gas is then collected and returned to the butyl facility.

A recorder-controller 38 is provided, for overall control of the process. The controller 38 is electrically connected to the pH measuring device 30 for the input of the pH to the controller 38. The controller 38 is electrically connected to a control means 39 associated with the variable control pump 22, so that the controller 38 can regulate and record the volume of alkali solution being supplied to reaction vessel 17 in accordance with signals received from the pH measuring device, so as to keep the pH in vessel 29 substantially constant. The recorder-controller 38 is also electrically connected to the gas volume recording means 37, so as to allow the controller 38 to receive measurements showing the volume of gas measured by means 37.

Figure 2:
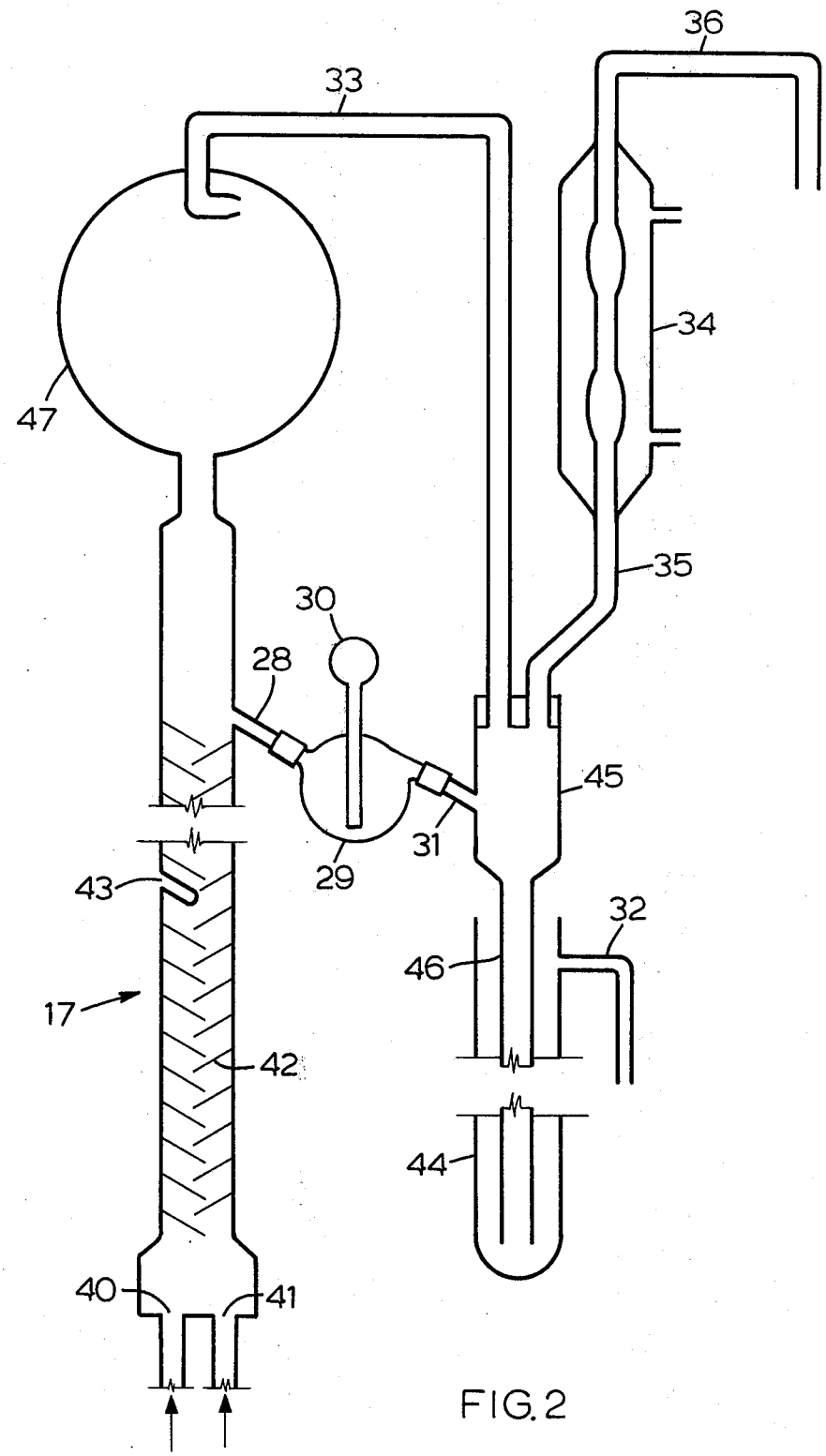
FIG. 2 is a diagrammatic cross-section of the reaction tube and associated parts of the apparatus used for conducting the process of FIG. 1.

The reaction vessel 17 and associated structure are shown diagrammatically in more detail in FIG. 2. The reaction vessel 17 has lower inlet ports 40, 41 for receiving the cold catalyst solution for analysis from line 16, and the steam and alkali mixture from lines 20, 21 respectively. The vessel 17 is provided with internal baffle plates such as 42 to promote reaction between ingredients therein. Near to its mid-point, the vessel 17 is provided with an inlet port 43 for receiving the temperature sensing means 23 previously referred to in FIG. 1.

The collection vessel 29, connected to reaction vessel 17 by means of outflow tube 28, takes the form of a small vessel into which a pH probe 30 is inserted. The size of the vessel is determined by the flow rates and is kept relatively small in order to increase the sensitivity to changes in pH in the aqueous phase therein. The collection vessel is provided with an overflow tube 31 feeding into collection funnel 45. Overflow control tube 44 is supplied with liquid from collection funnel 45 by means of a depending tube 46 which terminates near the bottom of overflow control tube 44. Liquid overflow control tube 44 flows to waste via line 32 and the liquid level in overflow control tube 44 is thereby controlled to the point at which line 32 connects with tube 44, the water in overflow control tube also providing a gas seal.

At its upper end, reaction vessel 17 terminates in a bulb 47. The gas outflow tube 33 communicates with the top of bulb 47 in such a manner as to discourage the carry over of liquid into the gas outflow tube. The other end of tube 33 communicates with the top of collection funnel 45. A further tube 35 leads from the top of collection funnel 45 to a condenser 34 so that outflow tube 33 and tube 35 are in communication to provide gas flow via the top of collection funnel 45. The temperature of condenser 34, which is cooled with cold water, is maintained substantially constant, at a level so that a major portion of the water vapor in the gas is condensed to the liquid phase and passed by tube 35 into collection funnel 45 to tube 44. This arrangement provides for the removal of water vapor from the gas stream so that the gas stream contains a substantially constant and low level of water vapor, which does not substantially interfere with or significantly contribute to the volume of gas measured. From condenser 34 there is provided further gas outflow tube 36, which proceeds to a gas volume measuring device 37, indicated on FIG. 1.

In operation, cold catalyst solution of aluminum trichloride in methyl chloride is fed from the butyl plant through inflow branch line 10 and lead-off line 16 into the bottom of reaction vessel 17. Simultaneously, steam is supplied to the bottom of reaction vessel 17 through line 20, and alkali solution is provided to the bottom of reaction vessel 17 via line 21. As the steam contacts the cold methyl chloride solution of catalyst, the temperature of the catalyst solution is raised so that the methyl chloride vapour flashes off. The vapour so formed is led out of the top of reaction vessel 17, via bulb 47, tube 33, funnel 45, tube 35, condenser 34, and line 36 to gas flow measuring device 37, from where the rate of flow of gas is recorded in controller 38. Any steam, moisture etc. which is carried over with the gaseous methyl chloride is condensed either in tube 33 or in condenser 34, so that the gas flow which reaches measuring device 37 is substantially totally flashed solvent.

As the solvent is flashed off in reaction tube 17, the aluminum trichloride from the catalyst reacts with the steam to form hydrogen chloride, which in turn reacts with the alkali supplied from line 21. The liquid solution of reaction products in water is fed from reaction vessel 17 via outflow tube 28 into collection vessel 29. The pH of the solution in vessel 29 is measured by pH meter 30, which provides a signal to controller 38, which in response to such signal controls the flow of alkali solution supplied by pump 22 to reaction vessel 17. The concentration of alkali solution supplied to pump 22 is kept constant at a suitable known value. The recorder-controller 38 records the rate of supply of the alkali solution, and computes this in conjunction with the rate of gas flow fed from the gas flow measuring device 37, suitably adjusted for the temperature and pressure of gas volume measurement, to give a continuous reading of catalyst concentration in the solution fed to the reaction vessel 17.

It will be appreciated that some considerable changes in temperatures of solution occur in reaction vessel 17. A catalyst solution from a butyl rubber polymerization facility is typically at a temperature of below about −70° C. In the process, this low temperature liquid stream is contacted rapidly and suddenly with a hot steam - alkali mixture, so as to flash off the volatile solvent (methyl chloride boils at about −24° C). If therefore the rate of supply of the steam to reaction vessel 17 becomes too low, the reaction tube 17 will very quickly freeze up. If this happens, temperature sensing device 23 operates to close valve 26 and shut off further catalyst solution supply through line 16 to reaction tube 17. As an alternative to using steam to unfreeze the vessel, nitrogen gas may be supplied via nitrogen supply line 19 and lead-off line 16 to reaction tube 17, so as to provide a gentle thawing of the reaction tube contents.

The methyl chloride solvent vapour is collected after passing through flow measuring device 37 for re-cycle in the butyl polymerization facility. Since methyl chloride is a toxic substance, losses of it in the process of the present invention are kept to a minimum.

Whilst the process of the invention has been specifically described with reference to determination of aluminum trichloride concentrations in methyl chloride solution in connection with a butyl rubber polymerization facility, it will be appreciated that it is of broader application. It can be adapted for use in monitoring the concentration of any aluminum halide in solution in a solvent which can be rapidly flashed off by contact with steam. Where aluminum trichloride is the aluminum halide being measured, the volatile solvent may, for example, be an alkyl halide, for example methyl chloride or ethyl chloride, or carbon disulphide. With respect to aluminum tribromide, the volatile solvent may be an alkyl halide or a lower alkane, such as butane, pentane and hexane, which solvents can be readily flashed off from solutions of aluminum tribromide therein on contact with steam.

The process of the present invention is also applicable to monitoring catalyst solution concentrations in other chemical processes where aluminum halide solutions in volatile solvents are used. These include various alkylation processes used in the hydrocarbon and petrochemical industries, where aluminum halides are used as Friedel-Craft reagents.

What is claimed is:
1. A process for determining the concentration of an aluminum halide in a solution of the aluminum halide in a volatile solvent, which comprises in combination the steps of:
   bringing the solution continuously into contact with hot water or steam to form an acidic reaction product which is proportional to the amount of aluminum halide, the quantity and temperature of the hot water or steam and the time of contact being sufficient to volatilize the solvent;
   contacting the reaction product continuously with an aqueous alkali solution of predetermined concentration;
   continuously controlling and measuring the rate of supply of said aqueous alkali solution so as substantially to neutralize the acidic reaction product and maintain the pH of the resultant reaction mixture within the pH range of 6.5 to 7.5 and thereby measure the amount of said acidic reaction product;
   and measuring the quantity of solvent volatilized, the concentration of the aluminum halide in the solvent being determined from the rate of supply of said aqueous alkali solution and the quantity of solvent volatilized.

2. The process of claim 1 wherein the aluminum halide solution, hot water or steam, and aqueous alkali solution are brought together in a reaction vessel equipped with temperature sensing and controlling means and the temperature in said reaction vessel is maintained within the range of 25° C to 90° C by adjusting the flow rate of the aluminum halide solution or of the hot water or steam.

3. The process of claim 2 wherein the pH of the resultant reaction mixture is measured continuously and adjustments are made to the flow rate of the aqueous alkali solution responsive to said pH measurements so as to maintain the pH of the resultant reaction mixture within the range of 6.5 to 7.5.

4. The process of claim 3 wherein the volatilized solvent is passed through a condenser means maintained at a substantially constant temperature so as to reduce the water vapor content of said volatilized solvent to a small, substantially constant level prior to measuring the volume of said volatilized solvent.

5. The process of claim 4 wherein the aluminum halide is aluminum trichloride, the volatile solvent is methyl chloride, ethyl chloride or carbon disulphide and the aqueous alkali solution is sodium hydroxide or potassium hydroxide.

6. The process of claim 4 wherein the aluminum halide is aluminum tribromide, the volatile solvent is one of methyl chloride, ethyl chloride, butane, pentane or hexane and the aqueous alkali solution is sodium hydroxide or potassium hydroxide.

7. The process of claim 5 wherein the concentration of the aluminum trichloride is from about 0.05 to 5 grams per 100 ml. of solution and the concentration of the aqueous alkali solution is from 0.02N to 0.5N.

* * * * *